United States Patent
Hinoue et al.

[11] Patent Number: 6,143,908
[45] Date of Patent: Nov. 7, 2000

[54] PROCESS FOR PREPARATION OF 1,3-DIOXOLANE-4-METHANOL COMPOUNDS

[75] Inventors: Kazumasa Hinoue, Amagasaki; Yoshiro Furukawa, Osaka, both of Japan

[73] Assignee: Daiso Co., Ltd., Osaka, Japan

[21] Appl. No.: 09/242,059

[22] PCT Filed: Sep. 9, 1997

[86] PCT No.: PCT/JP97/03165

§ 371 Date: Feb. 8, 1999

§ 102(e) Date: Feb. 8, 1999

[87] PCT Pub. No.: WO98/11087

PCT Pub. Date: Mar. 19, 1998

[30] Foreign Application Priority Data

Sep. 10, 1996 [JP] Japan .................................. 7-239024

[51] Int. Cl.[7] ...................... C07D 317/20; C07D 493/10
[52] U.S. Cl. ............................. 549/453; 549/331
[58] Field of Search ............................................. 549/453

[56] References Cited

U.S. PATENT DOCUMENTS 4,861,764  8/1989  Samour et al. .......................... 514/177

FOREIGN PATENT DOCUMENTS

| 268460 | 5/1988 | European Pat. Off. . |
|---|---|---|
| 1135727 | 5/1989 | Japan . |
| 6-62492 | 8/1994 | Japan . |
| WO 85/03704 | 8/1985 | WIPO .............................. C07C 59/10 |

OTHER PUBLICATIONS

Partali et al, Tetrahedron: Asymmetry, vol. 3, No. 1, pp. 65–72, 1992.

He et al., *Synthetic Communications*, 22(18), 2653–2658 (1992), "Studies on Carbohydrates X A New method for the Preparation of Isopropylidene Saccharides.".

Baer et al., J. Biol. Chem, "L–α–Glycerophosphoric Acid" 135, 321 (1940).

Jung et al., J. Am. Chem. Soc., "Total Synthesis of (R)–Glycerol Acetonide and the Antiepileptic and Hypotensive Drug (=)–γ–Amino–β–hydroxybutyric Acid (GABOB): Use of Vitamin C as a Chiral Starting Material", 1980, 102, 6304–6311.

Vänttinen et al., J. Chem. Soc. Perkin Trans., "Lipase–catalysed Transesterification in the Preparation of Optically Active Solketal," 1994, 3459–3463.

*Primary Examiner*—Bernard Dentz
*Attorney, Agent, or Firm*—Jacobson, Price, Holman & Stern, PLLC

[57] ABSTRACT

A process for preparing easily and economically a 1,3-dioxolane-4-methanol compound in a racemic form or an optically active form with high purity and in high yield.

The process comprises reacting an alkali metal or alkaline earth metal salt of an alcohol or a carboxylic acid with a halogenomethyl-1,3-dioxolane which is prepared by acetalizing a halogeno-1,2-propanediol of a formula (1) wherein X is a halogen atom, in an acid catalyst to conduct esterification or etherification, and then hydrolyzing the ester group and hydrogenolyzing the ether group to prepare a 1,3-dioxolane-4-methanol compound of a formula (5) wherein $R^1$ and $R^2$ are hydrogen atom, alkyl having 1 to 4 carbon atoms or phenyl, and $R^1$ and $R^2$ may form a cycloalkyl ring having 3 to 6 carbon atoms with the adjacent carbon atoms.

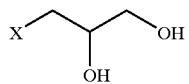

(1)

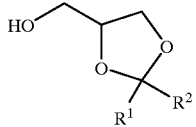

(5)

15 Claims, No Drawings

PROCESS FOR PREPARATION OF 1,3-DIOXOLANE-4-METHANOL COMPOUNDS

This application is a 371 of PCT/JP97/03165 filed Sep. 9, 1997.

TECHNICAL FIELD

The present invention relates to a process for preparation of 1,3-dioxolane-4-methanol compounds useful as an intermediate of medicines, agricultural chemicals, etc.

BACKGROUND ART 1,3-Dioxolane-4-methanol compounds are used as an intermediate of medicines, agricultural chemicals, etc. and following processes for preparation of them are known: (i) A process for preparation of them by reacting glycerin and an acetonide reagent (Synth. Commun., 22, 2653(1992), (ii) a process for preparation of them from mannitol (Biochem. Prep., 2, 31(1952)), (iii) a process for preparation of them from an ascorbic acid (J. Am. Chem. Soc., 102, 6304(1980), (iv) a process for preparation of them from serine (Japanese Patent Publication B No. 6-62492), (v) an optical resolution of them by using an enzyme (J. Chem. Soc., Perkin Trans. I 23, 3459(1994) and so on.

These processes, however, have industrially following disadvantages:

According to the process for preparation of them by reacting glycerin and an acetonide reagent of (i), a mixture of a compound acetalized between positions 1 and 2 and a compound acetalized between positions 1 and 3 is produced and it is hardly difficult to separate each compound from the mixture. According to the method of (ii), because chemically equivalent amount of lead tetraacetate or sodium periodic acid is used in case of cleavage of 1,2-diol compounds, it takes high costs and in case of preparing an optical isomer, only a (S)-form is obtained because only D-mannitol is present in nature. According to the process for preparation of them from L-ascorbic acid or D-isoascorbic acid of (iii), because chemically equivalent amount of lead tetraacetate or sodium periodic acid is used, it takes high costs like in case of (ii). According to the method from serine of (iv), in case of preparing an optical isomer, only a (R)-form is obtained because only a (L)-form is present in nature like in case of (ii) and furthermore in case of reduction of the carboxylic acid, the reagent which is difficult to be dealt with in mass production such as lithium aluminum hydride etc. must be used. According to the process by the biochemically optical resolution method of (v), purity of one of optical isomers is high, but purity of the other is low, and in some cases, in order to separate an optically active alcohol and an optically active ester which are prepared from a racemic alcohol, separation by column chromatography is necessary and therefore, it is not suitable for mass production. Furthermore, any process mentioned above contains many steps and is not practical. Therefore, a more efficient process for preparation of a 1,3-dioxolane-4-methanol was desired.

DISCLOSURE OF INVENTION

The present inventors engaged extensively in solving above problems, and found a novel process for preparing the above objective compound from a 3-halogeno-1,2-propanediol.

The present invention relates to a process for preparing a 1,3-dioxolane-4-methanol compound of the formula

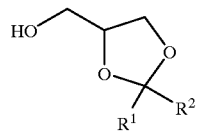

(5)

wherein $R^1$ and $R^2$ are the same or different and are hydrogen atom, alkyl having 1 to 4 carbon atoms or phenyl, and $R^1$ and $R^2$ may form a cycloalkyl ring having 3 to 6 carbon atoms with the adjacent carbon atoms, which is characterized in acetalizing a 3-halogeno-1,2-propanediol of the formula

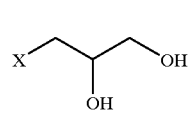

(1)

wherein X is halogen atom, with an acetalizing agent in the presence of an acid catalyst to prepare a 4-halogenomethyl-1,3-dioxolane of the formula

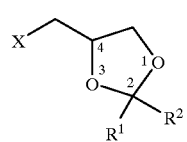

(2)

wherein $R^1$, $R^2$ and X are as defined above, and reacting it with an alkali metal salt or alkaline earth metal salt of a carboxylic acid or an alcohol of the formula

ROH      (3)

wherein R is acyl, aralkyl or allyl, to prepare a compound of the formula

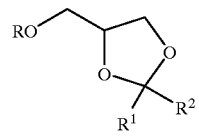

(4)

wherein R, $R^1$ and $R^2$ are as defined above, and when R is acyl in the formula (4), subjecting it to hydrolysis, and when R is aralkyl or allyl in the formula (4) subjecting it to hydrogenolysis in the presence of a reduction catalyst.

According to the present invention, in case of using an optically active 3-halogeno-1,2-propanediol as a starting material, there is obtained an optically active 1,3-dioxolane-4-methanol compound.

BEST MODE FOR CARRYING OUT THE INVENTION

The reaction of the present invention is schematically shown as follows.

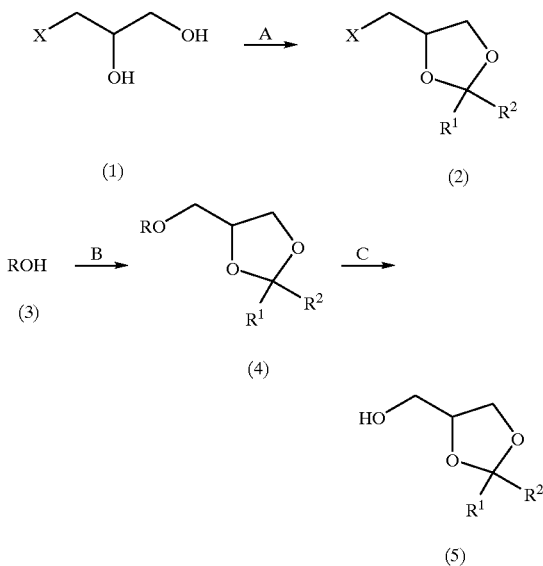

in the above formulae X, $R^1$, $R^2$ and R are as defined above.

Each step is explained in detail as follows.

Step(A)

A 4-halogenomethyl-1,3-dioxolane of the formula (2) is obtained by reacting a 3-halogeno-1,2-propanediol of the formula (1) with an acetalizing agent in the presence of an acid catalyst.

Preferable examples of the 3-halogeno-1,2-propanediols are 3-chloro-1,2-propanediol and 3-bromo-1,2-propanediol.

Examples of the acetalizing agents are ketones, such as acetone, diethyl ketone, benzophenone, cyclohexanone, etc., aldehydes, such as formaldehyde, acetoaldehyde, benzaldehyde, etc., dialkoxyacetals of ketones, such as 2,2-dimethoxypropane, 2,2-dimethoxypentane, etc., enol ethers of ketones, such as 2-methoxypropene etc. and so on.

For instances, when a compound of the formula (2) wherein $R^1$ and $R^2$ are hydrogen atom is prepared, formaldehyde is used, when a compound of the formula (2) wherein $R^1$ and $R^2$ are phenyl, benzophenone is used, when a compound of the formula (2) wherein $R^1$ and $R^2$ form a 6 membered ring together with the adjacent carbon atoms is prepared, cyclohexanone is used, and when a compound of the formula (2) wherein $R^1$ is phenyl and $R^2$ is hydrogen is prepared, benzaldehyde is used.

When a 1,3-dioxolane-4-methanol of the formula (5) wherein $R^1$ and $R^2$ are methyl is prepared, acetone, 2,2-dimethoxypropane and 2-methoxypropene are especially preferable as an acetalizing agent.

The examples of the acid catalysts are organic acids, such as p-toluenesulfonic acid, pyridinium p-toluenesulfonate, camphorsulfonic acid, etc., mineral acids such as hydrochloric acid, sulfuric acid, phosphoric acid, etc., and Lewis acid, such as, trifluoroborate etc. The amount of the acid catalyst is 0.05 to 0.1 mol equivalent to a 3-halogeno-1,2-propanediol.

The examples of solvents are ethers, such as diethyl ether, tetrahydrofuran, 1,4-dioxane, etc., halogen compounds, such as dichloromethane, dichloroethane, etc., acetone and so on.

The reaction temperature is from 0° C. to refluxing temperature of the solvent.

Step(B) (B-1) A 4-acyloxymethyl-1,3-dioxolane of the formula (4) in which R is acyl, is prepared by reacting a 4-halogenomethyl-1,3-dioxolane of the formula (2) which is prepared by step (A) with an alkali metal salt or alkaline earth metal salt of a carboxylic acid.

The examples of solvents are polar aprotic solvents, such as N,N-dimethylformamide, dimethyl sulfoxide etc., esters, such as ethyl acetate, butyl acetate, etc., ethers, such as tetrahydrofuran, 1,4-dioxane, 1,2-dimethoxyethane, diglyme, triglyme, diethlene glycol monomethyl ether, etc., ketones, such as acetone, methyl ethyl ketone, methyl isobutyl ketone, etc., nitriles, such as acetonitrile etc., halogen compounds, such as dichloromethane, 1,2-dichloroethane, etc., water and a mixture of these solvents.

Examples of the alkali metal salts or alkaline earth metal salts of a carboxylic acid are salts of an aliphatic carboxylic acid having 1 to 4 carbon atoms, salts of an aromatic carboxylic acid substituted or unsubstituted by an alkyl having 1 to 4 carbon atoms, nitro, cyano, a halogen atom, or an alkoxy having 1 to 4 hydrocarbon. Preferable the carboxylates are alkali metal salts or alkaline earth metal salts of benzoic acid and acetic acid, such as sodium benzoate, potassium benzoate, sodium acetate, potassium acetate, calcium benzoate, barium benzoate, etc.

The amount of the alkali metal salt or alkaline earth metal salt of a carboxylic acid is 1 to 3 moles per one mole of a 4-halogenomethyl-1,3-dioxolane, preferably 1 to 2 moles. To use it in excess does not affect the yield of the product, but it is not economical.

(B-2) A 4-alkoxymethyl-1,3-dioxolane of the formula (4) in which R is aralkyl or allyl, is prepared by reacting a 4-halogenomethyl-1,3-dioxolane of the formula (2) which is prepared by step (A) with an alkali metal salt or alkaline earth metal salt of an alcohol.

Examples of the alcohols are ones having aralkyl group or allyl group, especially preferably benzyl alcohol and allyl alcohol. The amount of the alcohol is 1 to 4 mole equivalent to a 4-halogenomethyl-1,3-dioxolane.

Examples of bases used in preparing the alkali metal salt or alkaline earth metal salt of an alcohol are alkali metal or alkaline earth metal carbonates, such as sodium carbonate, potassium carbonate, calcium carbonate, etc., alkali metal or alkaline earth metal hydroxides, such as sodium hydroxide, potassium hydroxide, calcium hydroxide, barium hydroxide, etc., alkali metal or alkaline earth metal hydrides, such as sodium hydride, lithium hydride, calcium hydride, etc., preferably alkali metal or alkaline earth metal hydroxides, such as sodium hydroxide, potassium hydroxide, calcium hydroxide, alkali metal or alkaline earth metal hydrides, such as sodium hydride, lithium hydride and calcium hydride.

Examples of solvents are polar aprotic solvents, such as N,N-dimethylformamide, dimethyl sulfoxide, etc., ethers such as tetrahydrofuran, 1,4-dioxane, 1,2-dimethoxyethane, etc., halogen compounds, such as dichloromethane, 1,2-dichloroethane, etc., water and a mixture of these solvents. The alcohols used as a starting material may serve as a solvent by using in excess.

The reactions in steps (B-1) and (B-2) proceed without catalyst, but the reactions are accelerated by adding iodo compounds, such as cesium iodide, sodium iodide, potassium iodide, etc., bromo compounds such as cesium bromide, sodium bromide, potassium bromide, etc., quaternary ammonium phase transfer salts such as terabutylammonium chloride, trimethylammonium bromide, etc., crown ether such as 18-Crown-6 etc., especially effective in case of a halogen atom in the formula (2) being chlorine atom. The preferable reaction promoters are an alkali metal bromide and an alkali metal iodide, especially sodium bromide, potassium bromide, sodium iodide and potassium iodide. Its amount is 0.05 to 1.1 mole equivalent to a 4-halogenomethyl-1,3-dioxolane. The reaction rate decreases in less than the amount and it is not practical.

Step (C)

A 1,3-dioxolane-4-methanol compound of the formula (5) is obtained by hydrolysis of a 4-acyloxymethyl-1,3-dioxolane of the formula (4) prepared by the above step (B-1) with a base in a solvent.

Examples of the solvents are alcohols such as methanol, ethanol, propanol, butanol, etc., ethers such as tetrahydrofuran, 1,4-dioxane, 1,2-dimethoxyethane, etc., water and a mixture of these solvents.

Examples of bases are alkali metal or alkaline earth metal carbonates, such as sodium carbonate, potassium carbonate, calcium carbonate, etc., alkali metal or alkaline earth metal hydroxides, such as sodium hydroxide, potassium hydroxide, calcium hydroxide, barium hydroxide, etc. The amount of the base is 1 to 3 mole equivalent to a 4-acyloxymethyl-1,3-dioxolane, preferably 1 to 1.5 mole equivalent. The reaction temperature is from 0° C. to refluxing temperature of the solvent.

A 1,3-dioxolane-4-methanol compound is obtained by catalytic hydrogenolysis of an 4-alkoxymethyl-1,3-dioxolane of the formula (4) prepared by the above step (B-2) under an atmosphere of hydrogen in a solvent.

The examples of the solvents are esters such as ethyl acetate, butyl acetate, etc., ethers, such as tetrahydrofuran, 1,4-dioxane, 1,2-dimethoxyethane, etc., ketones, such as acetone, methyl ethyl ketone, methyl isobutyl ketone, etc., alcohols such as methanol, ethanol, propanol, butanol, etc., water and a mixture of these solvents.

The catalysts are not limited as far as catalysts used in this field, but preferable ones are metal catalysts such as palladium, platinum, etc., and palladium is more preferable in view of the yield and economy. Especially about 5–10% palladium-carbon powder is better. The amount of the catalyst is preferably 0.5 to 50 weight percent per 4-alkoxymethyl-1,3-dioxolane. The reaction is usually carried out at room temperature under the atmosphere.

Thus obtained 1,3-dioxolane-4-methanol compound is prepared in good yield and high purity by usual purification methods, such as distillation in vacuo.

In case of using an optically active 3-halogeno-1,2-propanediol as a starting material, there is obtained an optically active 1,3-dioxolane-4-methanol compound. A 3-halogeno-1,2-propanediol with high optical purity (98% or more than 98%) is obtainable by methods described in Japanese Patent Publication B No. 4-73998, and No. 4-73999 which were filed by the present applicant.

According to the present invention, by using a (R)-3-halogeno-1,2-propanediol, there is obtained a (S)-1,3-dioxolane-4-methanol compound. A R-form compound is prepared in the same way. By using a 3-halogeno-1,2-propanediol with highly optical purity, there is obtained a 1,3-dioxolane-4-methanol compound with highly optical purity without marked racemization on the reaction.

The present invention is explained by the following examples, but it is not limited to these examples.

Examples 1 to 5, 7 and 6 are cases in variation of the halogen atoms (examples 1–5, 7: Cl, example 6: Br). Examples 1, 3, 5, 6, 2 and 4 are cases in variation of the carboxylates (example 1, 3, 5, 6: sodium benzoate, example 2, 4: sodium acetate). Examples 3, 4, 5 and 7 are cases used optically active 3-halogeno-1,2propanediols starting material. Example 1 and 5 are cases of a reaction being carried out with or without a reaction promoter. Example 7 is a case of using an metal salt of an alcohol.

EXAMPLE 1 p-Toluenesulfonic acid (1.79 g) was added to a mixture of 3-chloro-1,2-propanediol (104.49 g, 0.945 mol) and acetone (1500 ml) and the resulting mixture was stirred for 12 hours at 25° C. After completion of the reaction, acetone was removed in vacuo and the crude product was distilled to give 128.01 g of 4-chloromethyl-2,2-dimethyl-1,3-dioxolane (yield 89%, b.p. 45° C. at 5 mmHg).

Then, sodium bromide (43.01 g, 0.42 mol) and sodium benzoate (60.24 g, 0.42 mol) were added to a mixture of the above 4-chloromethyl-2,2-dimethyl-1,3-dioxolane (60.02 g, 0.39 mol) and N,N-dimethylformamide (600 ml) and the resulting mixture was stirred for 15 hours at 150° C. After cooling the salt was filtered off and N,N-dimethylformamide was removed in vacuo and water was added to the residue and extracted with toluene. The extract was washed with saturated brine, dried over anhydrous sodium sulfate and condensed in vacuo to give crude 4-benzoyloxymethyl-2,2-dimethyl-1,3-dioxolane (yield 90%).

Then sodium carbonate (32.22 g, 0.304 mol) was added to a mixture of the crude 4-benzoyloxymethyl-2,2-dimethyl-1,3-dioxolane (48.06 g, 0.203 mol) and water (100 ml) resulting mixture was stirred for 8 hours at 100° C. After cooling the reaction mixture was extracted with methylene chloride. The extract was washed with saturated brine, dried over anhydrous sodium sulfate and condensed in vacuo. The crude product was distilled to give 22.03 g of 2,2-dimethyl-1,3-dioxolane-4-methanol (yield 82%, b.p. 72° C. at 8 mmHg).

EXAMPLE 2

To a mixture of 4-chloromethyl-2,2-dimethyl-1,3-dioxolane (51.60 g, 0.343 mol) prepared by Example 1 and N,N-dimethylformamide (400 ml), sodium bromide (37.04 g, 0.36 mol) and sodium acetate (29.53 g, 0.36 mol) were added and the resulting mixture was stirred for 15 hours at 150° C. After cooling, the salt was filtered off and N,N-dimethylformamide was removed in vacuo. Water was added to the residue and it was extracted with toluene and the extract was washed with saturated brine, dried over anhydrous sodium sulfate and condensed in vacuo. The crude product was distilled to give 38.24 g of 4-acetoxymethyl-2,2-dimethyl-1,3-dioxolane (yield 64%, b.p. 81° C. at 12 mmHg).

Then sodium carbonate (40.63 g, 0.294 mol) was added to a mixture of 4-acetoxymethyl-2,2-dimethyl-1,3-dioxolane (34.18 g, 0.196 mol) and methanol (200 ml) and the resulting mixture was stirred for 8 hours at 25° C. After completion of the reaction the salt was filtered off and the filtrate was condensed in vacuo and water was added to the residue and extracted with methylene chloride. The extract was washed with saturated brine, dried over anhydrous sodium sulfate and condensed in vacuo. The crude product was distilled to give 23.12 g of 2,2-dimethyl-1,3-dioxolane-4-methanol (yield 89%, b.p. 72° C. at 8 mmHg).

EXAMPLE 3 p-Toluenesulfonic acid (0.86 g) was added to a mixture of (R)-3-chloro-1,2-propanediol (50.13 g, 0.454 mol, optical purity 98.7% e.e.) and acetone (660 ml) and the resulting mixture was stirred for 12 hours at 25C. After completion of the reaction, acetone was removed in vacuo and the crude product was distilled to give 58.11 g of (R)-4-chloromethyl-2,2-dimethyl-1,3-dioxolane (yield 85%, b.p. 63° C. at 25 mmHg).

Then, sodium bromide (24.70 g, 0.24 mol) and sodium benzoate (34.58 g, 0.42 mol) were added to a mixture of (R)-4-chloromethyl-2,2-dimethyl-1,3-dioxolane (36.48 g, 0.24 mol) and N,N-dimethylformamide (150 ml) and the resulting mixture was stirred for 15 hours at 150° C. After cooling the salt was filtered off and N,N-dimethylformamide was removed in vacuo and water was added to the residue and extracted with toluene. The extract was washed with saturated brine, dried over anhydrous sodium sulfate and condensed in vacuo to give 49.34 g of crude(R)-4-benzoyloxymethyl-2,2-dimethyl-1,3-dioxolane (yield 87%).

Then sodium carbonate (24.80 g, 0.234 mol) was added to a mixture of the crude 4-benzoyloxymethyl-2,2-dimethyl-1,3-dioxolane (36.95 g, 0.156 mol) and water (80 ml) and resulting mixture was stirred for 8 hours at 100° C. After cooling the reaction mixture was extracted with methylene chloride. The extract was washed with saturated brine, dried over anhydrous sodium sulfate and condensed in vacuo. The crude product was distilled to give 15.67 g of (S)-2,2-dimethyl-1,3-dioxolane-4-methanol (yield 76%, b.p. 72° C. at 8 mmHg, optical purity 98.6% e.e., specific rotation $[\alpha]_D^{20}$+11.1°(c=1,MeOH)).

EXAMPLE 4

Sodium bromide (57.93 g, 0.563 mol) and sodium acetate (46.18 g, 0.563 mol) were added to a mixture of (R)-4-chloromethyl-2,2-dimethyl-1,3-dioxolane (84.76 g, 0.563 mol) prepared by the same manner as Example 3 and N,N-dimethylformamide (800 ml) and the resulting mixture was stirred for 15 hours at 150° C. After cooling the salt was filtered off and N,N-dimethylformamide was removed in vacuo and water was added to the residue and extracted with toluene. The extract was washed with saturated brine, dried over anhydrous sodium sulfate and condensed in vacuo. The crude product was distilled to give 60.81 g of (R)-4-acetoxymethyl-2,2-dimethyl-1,3-dioxolane (yield 62%, b.p. 78° C. at 10 mmHg).

Then potassium carbonate (66.96 g, 0.485 mol) was added to a mixture of (R)-4-acetoxymethyl-2,2-dimethyl-1,3-dioxolane (56.32 g, 0.323 mol) and methanol (400 ml) and resulting mixture was stirred for 8 hours at 25° C. After completion of the reaction the salt was filtered off and the filtrate was condensed in vacuo. Water was added to the residue and the mixture was extracted with methylene chloride. The extract was washed with saturated brine, dried over anhydrous sodium sulfate and condensed in vacuo. The crude product was distilled to give 38.27 g of (S)-2,2-dimethyl-1,3-dioxolane-4-methanol (yield 87%, b.p. 65° C. at 3 mmHg, optical purity 97.5% e.e., specific rotation $[\alpha]_D^{20}$+10.87°(c=1,MeOH)).

EXAMPLE 5

Sodium benzoate (40.64 g, 0.282 mol) was added to a mixture of (R)-4-chloromethyl-2,2-dimethyl-1,3-dioxolane (42.38 g, 0.282 mol) prepared by the same manner as example 3 and N,N-dimethylformamide (400 ml) and the resulting mixture was stirred for 3 days at 150° C. After cooling the salt was filtered off and N,N-dimethylformamide was removed in vacuo and water was added to the residue and extracted with toluene. The extract was washed with saturated brine, dried over anhydrous sodium sulfate and condensed in vacuo to give 58.63 g of crude (R)-4-benzoyloxymethyl-2,2-dimethyl-1,3-dioxolane (yield 88%).

Then sodium carbonate (39.43 g, 0.372 mol) was added to a mixture of the crude (R)-4-benzoyloxymethyl-2,2-dimethyl-1,3-dioxolane (58.63 g, 0.248 mol) and water (130 ml resulting mixture was stirred for 8 hours at 100° C. After cooling the reaction mixture was extracted with methylene chloride. The extract was washed with saturated brine, dried over anhydrous sodium sulfate and condensed in vacuo. The crude product was distilled to give 21.96 g of (S)-2,2-dimethyl-1,3-dioxolane-4-methanol (yield 67%, b.p. 65° C. at 3 mmHg, optical purity 97.3 % e.e., specific rotation $[\alpha]_D^{20}$+10.84°(c=1,MeOH)

EXAMPLE 6 p-Toluenesulfonic acid (0.938 g) was added to a mixture of 3-bromo-1,2-propanediol (76.34 g, 0.493 mol) and acetone (720 ml) and the resulting mixture was stirred for 10 hours at 25° C. After completion of the reaction, acetone was removed in vacuo and the residues was distilled to give 78.81 g of 4-chloromethyl-2,2-dimethyl-1,3-dioxolane (yield 82%, b.p. 67° C. at 15 mmHg)

Then, sodium benzoate (50.44 g, 0.35 mol) were added to a mixture of 4-bromomethyl-2,2-dimethyl-1,3-dioxolane (58.52 g, 0.3 mol) and N,N-dimethylformamide (500 ml) and the resulting mixture was stirred for 15 hours at 150° C. After cooling the salt was filtered and N,N-dimethylformamide was removed in vacuo and water was added to the residue and extracted with toluene. The extract was washed with saturated brine, dried over anhydrous sodium sulfate and condensed in vacuo to give 64.5 g of crude 4-benzoyloxymethyl-2,2-dimethyl-1,3-dioxolane (yield 91%).

Sodium carbonate (16.53 g, 0.156 mol) was added to a mixture of the crude 4-benzoyloxymethyl-2,2-dimethyl-1,3-dioxolane (24.63 g, 0.104 mol) and water (50 ml) and resulting mixture was stirred for 8 hours at 100° C. After cooling the mixture was extracted with methylene chloride. The extract was washed with saturated brine, dried over anhydrous sodium sulfate and condensed in vacuo. The residue was distilled to give 10.86 g of 2,2-dimethyl-1,3-dioxolane-4-methanol (yield 79%, b.p. 68° C. at 6 mmHg).

EXAMPLE 7

Benzyl alcohol (32.90 g, 0.155 mol) was dropped under ice cooling in a suspension of 60% sodium hydride (5.88 g, 0.155 mol) and DMF (150 ml). After emission of hydrogen gas, sodium bromide (9.67 g, 0.094 mol) was added thereto. A DMF solution (15 ml) of (R)-4-chloromethyl-2,2-dimethyl-1,3-dioxolane (11.747 g, 0.078 mol) prepared by the same manner as Example 3 was dropped in it. The temperature was raised to 120° C. and the mixture was stirred for 15 hours. After completion of the reaction the reaction mixture was cooled on ice bath and neutralized with 6% hydrochloric acid. The solution was extracted with ethyl acetate. The organic layer was washed with water and with saturated brine, dried over anhydrous sodium sulfate and condensed in vacuo. The crude product was distilled to give 9.627 g of (S)-4-benzyloxymethyl-2,2-dimethyl-1,3-dioxolane (yield 54%, b.p. 112° C. at 0.3 mmHg).

10% Palladium-carbon (2.63 g) was added to (S)-4-benzyloxymethyl-2,2-dimethyl-1,3-dioxolane (9.267 g, 41.69 mmol) in ethanol (250 ml) and the mixture was stirred for 3 hours at 25° C. under an atmosphere of hydrogen. After the reaction was over, palladium-carbon was filtered off and the solvent was condensed in vacuo. The crude product was distilled to give 4.68 g of (S)-2,2-dimethyl-1,3-dioxolane-4-methanol (yield 85%, b.p. 65° C. at 3 mmHg, optical purity 97.5% e.e., specific rotation $[\alpha]_D^{20}$+10.84° (c=1, MeOH)).

According to the present invention, 1,3-dioxolane-4-methanol compounds are simply and economically prepared without expense reagents. A racemic or optically active compound of 1,3-dioxolane-4-methanol compounds is, if desired, prepared with high purity and in good yield.

What is claimed is:

1. A process for preparing a 1,3-dioxolane-4-methanol compound of the formula

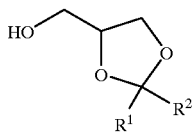
(5)

wherein $R^1$ and $R^2$ are the same or different and are hydrogen atom, alkyl having 1 to 4 carbon atoms or phenyl, and $R^1$ and $R^2$ may form a cycloalkyl ring having 3 to 6 carbon atoms with the adjacent carbon atoms, which is characterized in acetalizing a 3-halogeno-1,2-propanediol of the formula

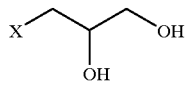
(1)

wherein X is a halogen atom, with an acetalizing agent in the presence of an acid catalyst to prepare a 4-halogenomethyl-1,3-dioxolane of the formula

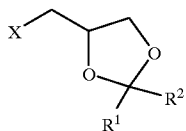
(2)

wherein $R^1$, $R^2$ and X are as defined above, and reacting it with an alkali metal salt or alkaline earth metal salt of an alcohol of the formula (3)

ROH (3)

wherein R is aralkyl or allyl, to prepare a compound of the formula

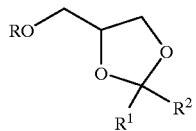
(4)

wherein R, $R^1$ and $R^2$ are as defined above, and subjecting it to hydrogenolysis in the presence of a reductive catalyst.

2. The process for preparing a 1,3-dioxolane-4-methanol compound claimed in claim 1, wherein a halogen atom in the formula (1) and (2) is chlorine atom or bromine atom.

3. The process for preparing a 1,3-dioxolane-4-methanol compound claimed in claim 1, wherein the acid catalyst is p-toluenesulfonic acid, pyridinium p-toluenesulfonate, camphorsulfonic acid or trifluoroborate.

4. The process for preparing a 1,3-dioxolane-4-methanol compound claimed in claim 1, wherein the acetalizing agent is a compound selected from ketones mentioned below, aldehydes mentioned below, dialkoxyacetals of ketones mentioned below and enol ethers of ketones mentioned below;

Ketones: acetone, diethyl ketone, benzophenone, cyclohexanone,

Aldehyde: formaldehyde, acetoaldehyde, benzaldehyde

Dialkoxyacetals of ketones: 2,2-dimethoxypropane, 2,2-dimethoxypentane,

Enol ethers of ketones: 2-methoxypropene.

5. The process for preparing a 1,3-dioxolane-4-methanol compound claimed in claim 4, wherein the acetalizing agent is a compound selected from acetone, 2,2-dimethoxypropane and 2-methoxypropene.

6. The process for preparing a 1,3-dioxolane-4-methanol compound claimed in claim 1, wherein the alkali metal salt or alkaline earth metal salt of an alcohol of the formula (3) is an alkali metal salt or alkaline earth metal salt of benzyl alcohol or allyl alcohol.

7. The process for preparing a 1,3-dioxolane-4-methanol compound claimed in claim 1, which is characterized in reacting a 4-halogenomethyl-1,3-dioxolane with an alkali metal salt or alkaline earth metal salt of an alcohol in the presence of a reaction promoter.

8. The process for preparing a 1,3-dioxolane-4-methanol compound claimed in claim 1, wherein the reduction catalyst is a palladium catalyst.

9. The process for preparing a 1,3-dioxolane-4-methanol compound claimed in claim 1, which is characterized in preparing a 1,3-dioxolane-4-methanol of the formula (5) in an optically active form from a 3-halogeno-1,2-propanediol of the formula (1) in an optically active form.

10. A process for preparing a 1,3-dioxolane-4-methanol compound of the formula

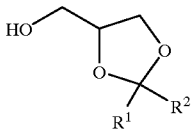
(5)

wherein $R^1$ and $R^2$ are the same or different and are a hydrogen atom, alkyl having 1 to 4 carbon atoms or phenyl, and $R^1$ and $R^2$ may form a cycloalkyl ring having 3 to 6 carbon atoms with the adjacent carbon, which is characterized in reacting a 4-halogenomethyl-1,3-dioxolane of the formula

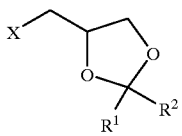
(2)

wherein $R^1$ and $R^2$ are the same as defined above and X is a halogen atom, with an alkali metal salt or alkaline earth metal salt of a carboxylic acid or an alcohol of the formula

ROH (3)

wherein R is acyl, aralkyl or allyl, in the presence of a reaction promoter to prepare a compound of the formula

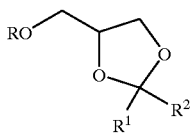
(4)

wherein R, $R^1$ and $R^2$ are as defined above,
and when R is acyl in the formula (4), subjecting it to hydrolysis, and when R is aralkyl or allyl in the formula (4) subjecting it to hydrogenolysis in the presence of a reductive catalyst.

11. The process for preparing a 1,3-dioxolane-4-methanol compound claimed in claim 10, wherein the reaction promoter is a compound selected from alkali metal bromides and alkali metal iodides.

12. The process for preparing a 1,3-dioxolane-4-methanol compound claimed in claim 11, wherein the alkali metal bromide or alkali metal iodide is a compound selected from sodium bromide, potassium bromide, sodium iodide and potassium iodide.

13. The process for preparing a 1,3-dioxolane-4-methanol compound claimed in claim 10, wherein the alkali metal salt or alkaline earth metal salt of an alcohol of the formula (3) is an alkali metal salt or alkaline earth metal salt of benzyl alcohol or allyl alcohol.

14. The process for preparing a 1,3-dioxolane-4-methanol compound claimed in claim 10, wherein the reduction catalyst is a palladium catalyst.

15. The process for preparing a 1,3-dioxolane-4-methanol compound claimed in claim 10, which is characterized in preparing a 1,3-dioxolane-4-methanol of the formula (5) in an optically active form from a 3-halogenomethyl-1,3-dioxolane of the formula (2) in an optically active form.

* * * * *